US012678213B2

(12) United States Patent
Ramin et al.

(10) Patent No.: US 12,678,213 B2
(45) Date of Patent: Jul. 14, 2026

(54) METHOD FOR MONITORING A HIGH RESISTANCE CONDITION AT AN ELECTROSURGICAL GENERATOR, ELECTROSURGICAL GENERATOR AND ELECTROSURGICAL GENERATOR SYSTEM

(71) Applicant: OLYMPUS WINTER & IBE GMBH, Hamburg (DE)

(72) Inventors: Daniel Ramin, Nuthetal (DE); Thomas Faehsing, Berlin (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 550 days.

(21) Appl. No.: 18/127,371

(22) Filed: Mar. 28, 2023

(65) Prior Publication Data

US 2023/0320774 A1     Oct. 12, 2023

Related U.S. Application Data

(60) Provisional application No. 63/324,317, filed on Mar. 28, 2022.

(51) Int. Cl.
*A61B 18/12* (2006.01)
*A61B 18/00* (2006.01)

(52) U.S. Cl.
CPC ..................... *A61B 18/1206* (2013.01); *A61B 2018/00827* (2013.01); *A61B 2018/00875* (2013.01); *A61B 2018/00892* (2013.01); *A61B 2018/00898* (2013.01)

(58) Field of Classification Search
CPC ........... A61B 2018/00827; A61B 2018/00875; A61B 2018/00892; A61B 2018/00898; A61B 2018/00988; A61B 18/1206
See application file for complete search history.

(56) References Cited

U.S. PATENT DOCUMENTS

2019/0254736 A1*  8/2019  Wham ............... A61B 18/1206

OTHER PUBLICATIONS

Jan. 21, 2023 Office Action issued in German Patent Application No. 10 2022 107 422.6.

* cited by examiner

*Primary Examiner* — Michael F Peffley
*Assistant Examiner* — Samantha M Good
(74) *Attorney, Agent, or Firm* — Oliff PLC

(57)     ABSTRACT
A method for monitoring a high resistance condition at an instrument terminal of an electrosurgical generator, which includes current and voltage measuring devices for determining a current and a voltage at the terminal to determine the high resistance condition, and includes a calculation device connected to the measuring devices which is configured to evaluate the determined current and voltage, including: determining a crest factor value from the current and/or voltage, wherein the crest factor value describes a ratio of a peak value to an effective value of the current and/or voltage; comparing the determined crest factor value with a comparison value by means of a comparison device, wherein the comparison value is stored in a data storage device; and signaling a high resistance condition with a signaling device when the determined crest factor reaches or exceeds the predetermined crest factor comparison value. Also, an electrosurgical generator and electrosurgical generator system.

10 Claims, 6 Drawing Sheets

$$K_S = \frac{X_{peak}}{X_{RMS}} \approx 1.5$$

$$K_S = \frac{X_{peak}}{X_{RMS}} \approx 2$$

METHOD FOR MONITORING A HIGH RESISTANCE CONDITION AT AN ELECTROSURGICAL GENERATOR, ELECTROSURGICAL GENERATOR AND ELECTROSURGICAL GENERATOR SYSTEM

BACKGROUND

The invention relates to a method for monitoring a high resistance condition at an instrument terminal of an electrosurgical generator. The invention also relates to an electrosurgical generator adapted to monitor a high resistance condition at an instrument terminal of the electrosurgical generator. The invention also relates to electrosurgical generator system comprising an electrosurgical generator.

Electrosurgical generators for operating electrosurgical instruments are generally known. Such generators are used as power supply for electrosurgical instruments connected the generator. Such generators are also used for monitoring the correct operation of the connected electrosurgical instrument.

When using electrosurgical instruments that are powered by electrosurgical generators, it may happen that electrosurgical instruments are not connected properly with the generator. Furthermore, it may happen that a cable break of the electrosurgical instrument occurs, due to an accidental bend of the connection line of the electrosurgical instrument.

In order to detect such undesirable conditions, it is known to use open circuit detections for monitoring a resistance value at the instrument terminal of the electrosurgical generators.

Typical and known open circuit detections usually measure the resistance value at the instrument terminals of the generator. The resistance value for alternating current (AC) applications is also known as impedance. The principle of this type of detection is that the resistance value at the instrument terminal is measured and the measured value is compared with a predefined resistance value, e.g. 4000 Ohm. If the measured resistance value reaches or exceeds the predefined resistance value, an open circuit is detected and, if necessary, is indicated to the operator of the generator.

However, a solely resistance value monitoring for detecting a high resistance condition at the generator has disadvantages, in particular when an AC-based generator is used that generates an alternating current for supplying the connected electrosurgical instrument.

In the case of capacitive loads connected to the generator, which are formed e.g. by the instrument cable, it may happen that the current or voltage generated by the generator carries strong harmonics, which distort the resistance measuring. Thus, a measurement of the phase shift between voltage and current can be distorted. Especially with small currents, a large inaccuracy can be observed. In general, the current and voltage waveforms are very poor in case of unfavorable loads. The phase values of the current and voltage are sometimes even completely unusable, which means that the measurement method is physically not usefully applicable for determining said high resistance condition reliable.

Accordingly, with a solely resistance or impedance monitoring an uncertain and unreliable open circuit detection is provided.

SUMMARY

It is an object of the present invention to provide a solution for increasing the reliability of a high resistance condition monitoring. In particular, it is an object of the present invention to provide a solution, which provides a reliable detection of open circuits, no contact of an electrosurgical instrument with a tissue or a reliable detection of an interrupted connection line (cable break).

According to a first aspect of the invention a method for monitoring a high resistance condition at an instrument terminal of an electrosurgical generator according to claim 1 is suggested.

The electrosurgical generator is used for driving an electrosurgical instrument. The electrosurgical generator supplies said instrument with electrical power, for instance, from an electrical supply grid or from an electrical storage device, such as a battery.

The electrosurgical generator comprises an instrument terminal for connecting and electrically supplying the electrosurgical instrument. The instrument terminal can be understood as a connector or port. In operation, the instrument is connected to the terminal in order to provide an electrical connection between the instrument and the generator. The generator is configured to supply the instrument with current or voltage electrically. The generator is connected for that purpose for example with an electrical supply grid and includes a power converter for power supply of the instrument. The power converter can also be referred to as switching device. Power converters are generally known. Power converters for converting alternating current to direct current are known as rectifiers. Power converters for converting direct current to alternating current are known as inverted rectifier or inverters. Power converters for converting one AC current to another AC current are known as frequency converters. Power converters for converting a direct current to another direct current are known as DC-to-DC converters. The generated alternating current or generated direct current can be higher, lower or inverted depending on the design of the converter or the requirements of the electrical load. Furthermore, an alternating current implies an alternating voltage, since voltage is causing the current.

The high resistance condition at the instrument terminal can also be understood as high ohmic condition or in case of an AC application as high impedance condition. The impedance is also known as AC resistance. Thus, it is suggested to identify the said high resistance condition at the instrument terminal of the generator.

The electrosurgical generator includes for that purpose a current measuring device for determining a current at the instrument terminal and a voltage measuring device for determining a voltage at the instrument terminal in order to determine the high resistance condition. The current measuring device can also be understood as a current meter or means for measuring the electrical current at the instrument terminal of the generator. The voltage measuring device can also be understood as voltmeter or means for measuring the electrical voltage at the instrument terminal of the generator. The current measuring devices and/or voltage measuring device is preferably adapted to record or to track the current and/or voltage generated at terminal contacts of the instrument terminal over time, in particular as a voltage waveform or current waveform. The current and/or voltage measuring device measures the current and/or voltage in single-phase or multi-phase, depending on how many electrical connections lines the instrument terminal includes.

The electrosurgical generator further includes a calculation device connected to the current measuring device and voltage measuring device. The calculation device is configured for data exchange with the measuring devices. The calculation device is also configured to evaluate the determined current and the determined voltage. The calculation device is for example a processing unit of the electrosurgical generator such as a CPU or a microcontroller or the like. The calculation device can also be understood as an analyzing device or evaluation unit. The calculation device is preferably adapted to track or record waveforms of the determined current and/or the determined voltage and to analyze the recorded waveforms. For example, the calculation device is adapted to determine a phase angle or a phase shift between the generated voltage and the generated current, or it is to adapted to determine an amplitude or a frequency of the determined voltage and/or current. The calculation device is thus adapted for data analysis of the current and/or the voltage, for example by means of a program code or algorithm that is implemented in the generator.

The method for monitoring the high resistance condition at the instrument terminal of the electrosurgical generator comprises the step of determining a crest factor value from the determined current and/or the determined voltage with the calculation device, wherein the crest factor value describes a ratio of a peak value to an effective value of the determined current and/or the determined voltage. The crest factor is a parameter of a waveform, such as alternating current, showing the ratio of peak values to the effective value. The crest factor indicates how strongly peaks are present in a waveform, or in the present case, how strongly the peaks of the determined current and/or determined voltage are. A crest factor of 1 indicates for example no peaks, such as direct current or a square wave. Higher crest factors indicate peaks. The crest factor is equal or greater than 1. In other words, the crest factor value describes the peak amplitude of the determined current and/or voltage waveform divided by the root mean square (RMS) value of the waveform. This ratio can be expressed by the formula $K_S=X_{peak}/X_{RMS}$, with X being a voltage U or a current I, for example $I_m$ or $U_m$.

The method for monitoring the high resistance condition at the instrument terminal of the electrosurgical generator further comprises the step of comparing the determined crest factor value with a crest factor comparison value by means of a comparison device of the electrosurgical generator, wherein the crest factor comparison value is stored in a data storage device of the electrosurgical generator for performing the comparison. It is thus suggested to compare the determined crest factor value with a comparison value, namely the crest factor comparison value. The crest factor comparison value can also be understood as a threshold value or threshold limit or reference value. The comparison of the crest factor value with the crest factor comparison value is performed by means of a comparison device, which is for example a hardware or software implemented logic circuit that is implemented in the generator and that is adapted to compare the determined crest factor value with the crest factor comparison value. The comparison device can also be understood as a logic circuit or processing unit with a program code. The comparison device and the calculation device may be integrally formed as one device. The data storage device may also be understood as a memory unit or data storage. The data storage device is preferably a non-volatile data storage device, which stores the crest factor comparison value independently of the operating state of the electrosurgical generator. The data storage device may also be used to store a first and second resistance comparison value.

The method for monitoring the high resistance condition at the instrument terminal of the electrosurgical generator further comprises the step of signaling a high resistance condition with a signaling device of the electrosurgical generator when the determined crest factor reaches or exceeds the predetermined crest factor comparison value. The signaling device is a device that is adapted to generate a warning indication, such as an optical or acoustical warning indication. The warning indication may be indicated at the generator. Thus, the high resistance condition is indicated, when crest factor value reaches or exceeds the predetermined crest factor comparison value, which can be expressed by the formula $K_S \geq K_V$. The high resistance condition may be signaled as a warning indication by means of an acoustic signaling device and/or an optical signaling device. For example, a colored LED could be activated, when the crest factor value reaches or exceeds the predetermined crest factor comparison value. A second example is that a message on a user display of the generator could be displayed as warning indication. A third example is that an acoustic sound signal could be played as warning indication. The signaling thus preferably includes signaling the high resistance condition by means of a warning indication.

Due to a bad waveform of the open circuit, a deformation of the voltage waveform may occur. This deformation leads to a crest factor ($K_S=U_{peak}/U_{RMS}$), which is different from the crest factor in the normal undistorted case. In this case, a deformation and an increased crest factor is visible. For example, in a distorted case, a continuous sine waveform has a crest factor of approx. 2 at open load and in the undistorted case with a normal load a typical crest factor of approx. 1.5 is present.

It was discovered that a consideration of the crest factor for an open circuit detection increases the reliability of the detection, because the crest factor is less sensitive to poor current and/or voltage waveforms, for example compared to a pure resistance or impedance monitoring. Thus, a reliable detection of open circuits, no contact of the electrosurgical instrument with tissue or a reliable detection of an interrupted connection line (cable break) is provided. Furthermore, since voltage and/or current measuring devices are often already part of the electrosurgical generators, a very simple implementation due to already existing sensors is also provided. Thus, a reliable detection of a high resistance or impedance condition especially for bad waveforms is provided.

Preferably the method comprises the additional step of determining the current and the voltage at the instrument terminal by means of the current measuring device and the voltage measuring device. This step can also be understood as measuring step. Determining can also be understood as measuring. As measuring device typical voltmeter and current meter can be used.

Preferably, the method comprises the additional steps of determining a resistance value from the determined current and/or the determined voltage with the calculation device. It follows that the calculation device is adapted to determine the resistance value from the the determined current and/or the determined voltage. The resistance value can be understood as the determined value for the electrical resistance or electrical impedance. The resistance value can be determined by means of a software calculation or by means of a hardware logic circuit. In both cases the resistance or impedance follows from ohm's law. If the voltage and the current are determined and known, the resistance can be determined, for example by calculating $R=U/I$ or the impedance can be determined by $Z=|Z| e^{j\varphi}=Z(\cos \varphi + j \sin \varphi)$ or $Z=R+j X$, wherein R is the resistance and X is the reactance and $\varphi$ is the phase change. Thus, it is suggested to determine the resistance with the calculation device from the measured voltage and/or current at the instrument terminal.

The next preferred additional step is comparing the determined resistance value with a first resistance comparison value and/or a second resistance comparison value with the comparison device, wherein the first resistance comparison value defines a lower limit for the determined resistance and the second resistance comparison value defines an upper limit for the determined resistance, and wherein for performing the comparison the first resistance comparison value and/or the second resistance comparison value is stored in the data storage device. It is thus suggested to compare the determined resistance value with two comparison values, namely with the first and second resistance comparison value. The first resistance comparison value can be understood as a threshold value or threshold limit. The first resistance comparison value is provided as a lower limit for the determined resistance value. The second resistance comparison value can also be understood as a threshold value or threshold limit. The second resistance comparison value is provided as an upper limit for the determined resistance value. Both resistance comparison values can be stored in the data storage device as described before. The two values are thus available for the comparison as data or as a reference value.

The next preferred additional step is signaling the high resistance condition with a signaling device of the electrosurgical generator when the determined crest factor reaches or exceeds the predetermined crest factor comparison value and when the determined resistance value is between the first resistance comparison value and the second resistance comparison value. It is thus suggested to combine the resistance monitoring and the crest factor monitoring. Thus an open circuit is preferably indicated, when the determined crest factor reaches or exceeds the predetermined crest factor comparison value and when the determined resistance value is between the first resistance comparison value and the second resistance comparison value, which can be expressed by the formula $((K_S \geq K_V)$ and $(R_{V1} < R_m < R_{V2}))$. This embodiment is particular preferred because a combination of both methods is particularly reliable. The "and"-expression in the formula indicates the Boolean expression that both conditions $(K_S \geq K_V)$ and $(R_{V1} < R_m < R_{V2})$ have to be fulfilled.

Preferably signaling the high resistance condition is performed when the determined resistance value exceeds the second resistance comparison value. Thus an open circuit is further preferred indicated, when the determined crest factor reaches or exceeds the predetermined crest factor comparison value and when the determined resistance value is between the first resistance comparison value and the second resistance comparison value and the determined resistance exceeds the second resistance comparison value, which can be expressed by the formula $[[((K_S \geq K_V)$ and $(R_{V1} < R_m < R_{V2}))]$ or $[R_m > R_{V2}]]$. It is thus suggested to indicate the high resistance condition, when the determined resistance value exceeds the second resistance comparison value. It was discovered that the crest factor determination can be stopped or deactivated, when the resistance value is too high.

Preferably, the first resistance comparison value is in a resistance range between 1000 ohms to 2000 ohms. Further preferred the first resistance comparison value is in a resistance range between 1250 ohms to 1750 ohms. In a further preferred embodiment, the first resistance comparison value is about 1500 ohms.

Preferably, the second resistance comparison value is in a resistance range between 3000 ohms to 5000 ohms. Further preferred the second resistance comparison value is in a resistance range between 3250 ohms to 3750 ohms. In a further preferred embodiment, the second resistance comparison value is about 3500 ohms.

To avoid false detections the detection of the high resistance condition should start from a fixed lower resistance value, namely the first resistance comparison value, e.g. 1500 Ohm, and should be deactivated from an upper value, namely the second resistance comparison value, e.g. 3500 Ohm.

Preferably, the crest factor comparison value is at least $1.25*\sqrt{2}(K_V > 1.25*\sqrt{2})$ for a substantially sinusoidal current generated by the electrosurgical generator at the instrument terminal. In a further preferred embodiment, the crest factor comparison value is 1.8. In case the determined current measured at the output of the instrument terminal has an ideal sinus waveform, the crest factor value is $\sqrt{2}$. Thus a crest factor of $\sqrt{2}$ describes an undistorted waveform without any harmonics in this case. When harmonics are present in the sinusoidal waveform, the crest factor will increase. It is suggested that the high resistance condition will be indicated, when the crest factor is 25% greater compared the undistorted case. It was discovered that a derivation over 25% of the distorted case to the undistorted case is a reliable trade-off between robustness and sensitivity, when monitoring the high resistance condition.

Due to the bad waveform of the open circuit, a deformation of the voltage waveform may occur. This deformation leads to a crest factor $(K_S = U_{peak}/U_{RMS})$ which is clearly different from the normal crest factor. In this case, an increased factor is visible, practically this means for a continuous sine waveform a crest factor of approx. 2 at open and in the normal load range a typical crest factor of approx. 1.5. The difference of at least 25%, for example 33%, makes a reliable detection of an open circuit possible, if necessary together with a simultaneous monitoring of the resistance value.

Preferably, the crest factor comparison value is at least $1.25*\sqrt{3}(K_V > 1.25*\sqrt{3})$ for a substantially triangular current generated with the electrosurgical generator at the instrument terminal. In case the determined current measured at the output of the instrument terminal has an triangular waveform, the crest factor value is $\sqrt{3}$. Thus a crest factor of $\sqrt{3}$ describes an undistorted waveform without any harmonics in this case. When harmonics are present in the triangular waveform, the crest factor will increase. It is suggested that the high resistance condition will be indicated, when the crest factor is 25% greater compared the undistorted case. It was discovered that a derivation over 25% of the distorted case to the undistorted case is a reliable trade-off between robustness and sensitivity, when monitoring the high resistance condition.

Preferably, the crest factor comparison value is at least $1.25*\sqrt{1}(K_V > 1.25*\sqrt{1})$ for a substantially rectangular current generated with the electrosurgical generator at the instrument terminal. In case the determined current measured at the output of the instrument terminal has an rectangular waveform, the crest factor value is $\sqrt{1}$. Thus a crest factor of $\sqrt{1}$ describes an undistorted waveform without any harmonics in this case. When harmonics are present in the rectangular waveform, the crest factor will increase. It is suggested that the high resistance condition will be indicated, when the crest factor is 25% greater compared to the undistorted case. It was discovered that a derivation over 25% of the distorted case to the undistorted case is a reliable trade-off between robustness and sensitivity, when monitoring the high resistance condition.

Preferably, the signaling device comprises an acoustic signaling device for outputting an acoustic signal to acoustically signal the high resistance condition detected at the instrument terminal when at least the determined crest factor reaches or exceeds the crest factor comparison value. An example for an acoustical warning indication that is generated by of the means acoustic signaling device is a sound signal, which is generated by means of a sound generator, such as a speaker.

Preferably, the signaling device comprises an optical signaling device for outputting an optical signal or message to optically signal the high resistance condition detected at the instrument terminal when at least the determined crest factor reaches or exceeds the crest factor comparison value. An example for an optical warning indication that is generated by of the means optical signaling device is a warning message shown on a display of the generator or an optical signal, which is generated by means of a colored lamp or LED at the generator, for instance a yellow or red LED is activated, when the crest factor comparison value is reached.

Preferably, the electrosurgical generator is a high frequency generator and the determined current and the determined voltage are alternating quantities. Further preferred the determined current is a periodic AC-current and the voltage is a periodic AC-voltage. As a high frequency generator a generator is understood that is adapted to generate a current with a frequency over 200 KHz.

Preferably, the electrosurgical generator comprises a plurality of instrument terminals, and the high resistance condition of each instrument terminal is monitored by determining the current and/or the voltage at each instrument terminal, and at least determining a crest factor for each instrument terminal, and comparing each crest factor with a or the crest factor comparison value. It is thus suggested to monitor the high resistance condition of all instrument terminals of the electrosurgical generator, preferably independently. Also, the resistance value can be analog determined for each instrument terminal.

According to a first further aspect of the invention an electrosurgical generator adapted to monitor a high resistance condition at an instrument terminal of the electrosurgical generator, wherein the instrument terminal is adapted for connecting and electrically supplying the electrosurgical instrument, wherein the electrosurgical generator includes a current measuring device for determining a current at the instrument terminal and a voltage measuring device for determining a voltage at the instrument terminal in order to determine the high resistance condition, and wherein the electrosurgical generator includes a calculation device which is connected to the current measuring device and voltage measuring device and which is configured to evaluate the determined current and the determined voltage, wherein the calculation device is adapted to determine a crest factor value from the determined current and the determined voltage, wherein the crest factor value describes a ratio of a peak value to an effective value of the determined current and/or the determined voltage, and wherein the electrosurgical generator comprises a comparison device for comparing the determined crest factor value with a crest factor comparison value, wherein the crest factor comparison value is stored in a data storage device of the electrosurgical generator for performing the comparison, and wherein the electrosurgical generator comprises a signaling device for signaling the high resistance condition, wherein the high resistance condition is signaled with the signaling device when the determined crest factor reaches or exceeds the predetermined crest factor comparison value.

Thus, an electrosurgical generator is suggested that is adapted to perform the previously described method for monitoring a high resistance condition at an instrument terminal of the instrument terminal. The electrosurgical generator accordingly comprises at least one instrument terminal, a current measuring device, a voltage measuring device, a calculation device, a comparison device, a data storage device and a signaling device, preferably as described hereinbefore or hereinafter.

It was discovered that a consideration of the crest factor for an open circuit detection increases the reliability of the detection, because the crest factor is less sensitive to poor current and/or voltage waveforms than a pure resistance or impedance monitoring. Thus, a reliable detection of open circuits, no contact of the electrosurgical instrument with tissue or a reliable detection of an interrupted connection line (cable break) is provided. Furthermore, since voltage and/or current measuring devices are often already part of the electrosurgical generators, a very simple implementation due to already existing sensors is also provided. Thus, a reliable detection of a high resistance or impedance condition especially for bad waveforms is provided.

As to the advantages, preferred embodiments and details of this further aspect and its preferred embodiments, reference is made to the corresponding advantages, preferred embodiments and details described above.

Preferably, the calculation device is also adapted for determining a resistance value from the determined current and/or the determined voltage, and the comparison device is adapted to for comparing the determined resistance value with a first resistance comparison value and/or a second resistance comparison value with the comparison device, wherein the first resistance comparison value defines a lower limit for the determined resistance and the second resistance comparison value defines an upper limit for the determined resistance, and wherein for performing the comparison the first resistance comparison value and/or the second resistance comparison value is stored in the data storage device; and the high resistance condition is signaled with the signaling device when the determined crest factor reaches or exceeds the predetermined crest factor comparison value and when the determined resistance value is between the first resistance comparison value and the second resistance comparison value, and preferably the high resistance condition is additionally signaled when the determined resistance exceeds the second resistance comparison value. It is thus suggested to combine the resistance monitoring and the crest factor monitoring. Thus an open circuit is preferably indicated, when the determined crest factor reaches or exceeds the predetermined crest factor comparison value and when the determined resistance value is between the first resistance comparison value and the second resistance comparison value, which can be expressed by the formula $((K_S \geq K_V)$ and $(R_{V1} < R_m < R_{V2}))$. This embodiment is particular preferred because a combination of both methods is particularly reliable. The "and"-expression in the formula indicates the Boolean expression that both conditions $(K_S \geq K_V)$ and $(R_{V1} < R_m < R_{V2})$ have to be fulfilled.

Preferably, the electrosurgical generator is adapted for performing the method according to one of the preceding embodiments.

Preferably, the electrosurgical generator is a high frequency generator and the determined current and the determined voltage are alternating quantities. Further preferred the determined current is a periodic AC-current and the voltage is a periodic AC-voltage.

According to a second further aspect of the invention an electrosurgical generator system is suggested, wherein the electrosurgical generator comprises an electrosurgical generator, wherein the electrosurgical generator comprises at least one instrument terminal for connecting and electrically supplying the electrosurgical instrument, wherein in operation of the electrosurgical generator system the electrosurgical instrument is connected to the instrument terminal, wherein the electrosurgical generator is configured according to any one of preceding or following embodiments and/or is adapted to perform the method according to any one of the preceding or following embodiments. The electrosurgical generator system thus comprises the electrosurgical generator and the electrosurgical instrument that is connected to the instrument terminal.

As to the advantages, preferred embodiments and details of this further aspect and its preferred embodiments, reference is made to the corresponding advantages, preferred embodiments and details described above.

Preferred embodiments shall now be described with reference to the attached figures, in which

BRIEF DESCRIPTION OF THE DRAWINGS

In the figures, elements with the same or comparable functions are indicated with the same reference numerals.

DETAILED DESCRIPTION

Figure 1:
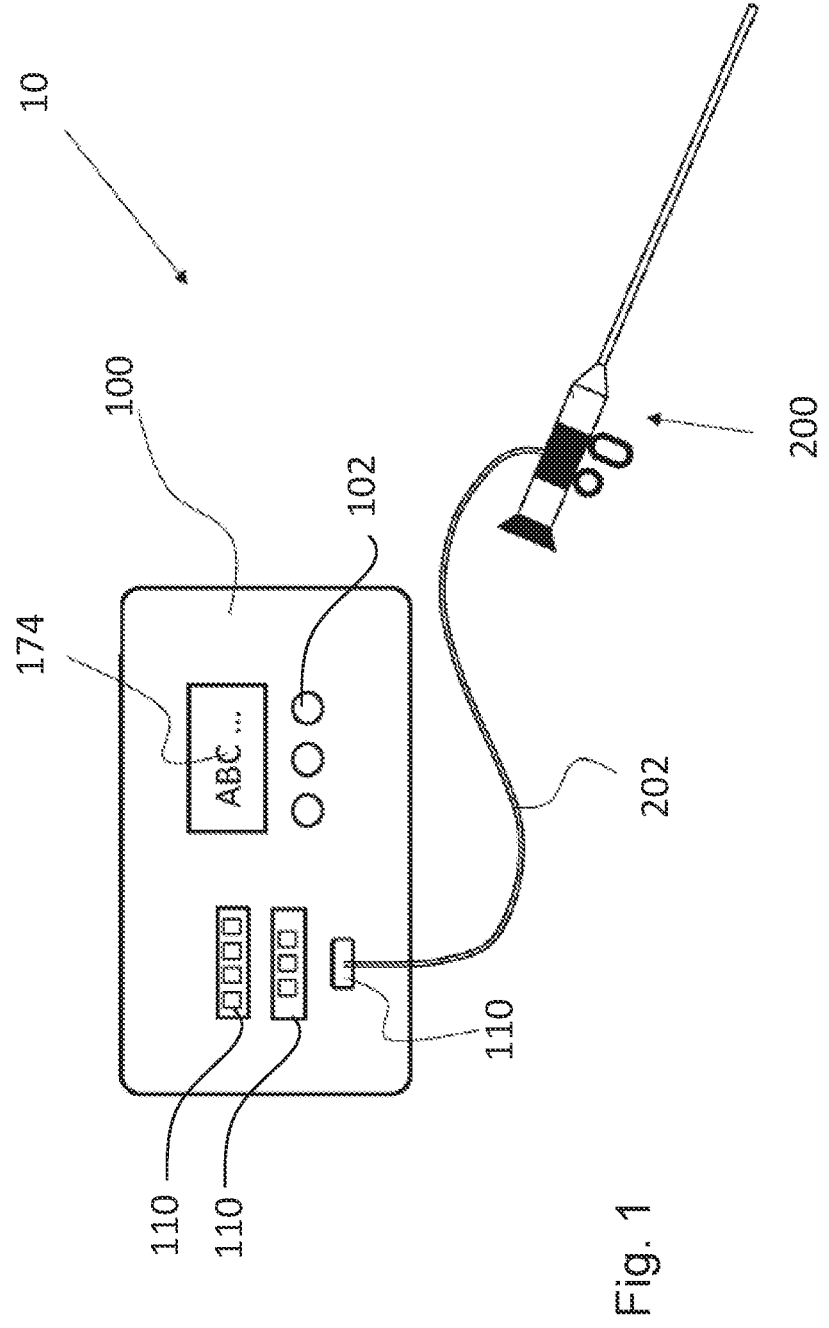
FIG. 1 shows an electrosurgical generator system with an electrosurgical generator and an electrosurgical instrument connected to the electrosurgical generator according to an embodiment.

FIG. 1 shows an electrosurgical generator system 10 with an electrosurgical generator 100 and an electrosurgical instrument 200 connected to the electrosurgical generator 100. The electrosurgical instrument 200 is connected with the electrosurgical generator 100 at the instrument terminal 110 by mean of a connection line 202. The connection line 202 may include supply lines and a data transfer line, which are not shown in FIG. 1. The supply line are used to supply the instrument 200 with electrical power and the data transfer line is used to exchange data between the instrument and the generator. The generator may also include several instrument terminals, for example a neutral instrument terminal, a unipolar instrument terminal and a bipolar instrument terminal. The electrosurgical instrument 200 includes a shaft having an active electrode at the end of the shaft. The shaft is attached to a handle of the electrosurgical instrument. The generator 100 includes a display 174 for displaying text and/or symbols and/or graphics, which is adapted to display an optical warning indication. The generator 100 also includes an operating device 102 which are shown as three buttons. The operating device 102 may also be a touch display or the like. The electrosurgical generator 100 is used for operating the electrosurgical instrument 200.

Figure 2:
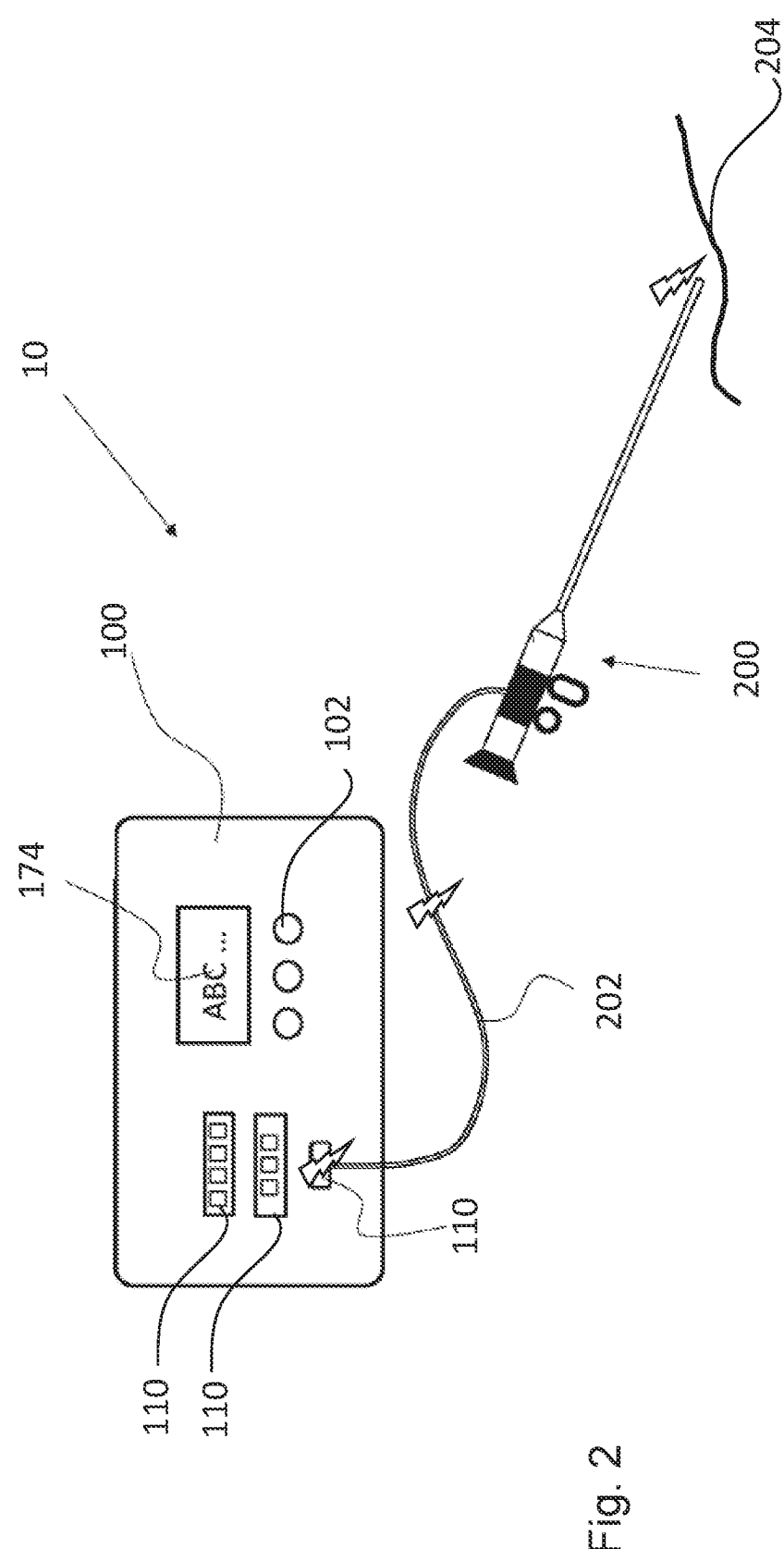
FIG. 2 shows exemplary where the high impedance condition may have its origin when operation an electrosurgical generator system.

FIG. 2 shows exemplary where the high impedance condition may have its origin when operation an electrosurgical generator system. FIG. 2 shows the electrosurgical generator system as shown in FIG. 1. A high impedance condition may be cause by a faulty connection of the connection line 202 of the instrument 200 with the instrument terminal 110, which is indicated by a lightning symbol. Furthermore, it might happen that a cable break of the electrosurgical instrument 200 occurs, due to an accidental bend of the connection line 202 of the electrosurgical instrument 200. This is indicated with a lightning symbol at the connection line 202. Furthermore, a high impedance condition may occur, when the active electrode at the end of the shaft of the instrument 200 is not in contact with the tissue 204 that partially conducts electrical current. This is indicated with a lightning symbol at the end of the active electrode of the instrument 200.

Figure 3:
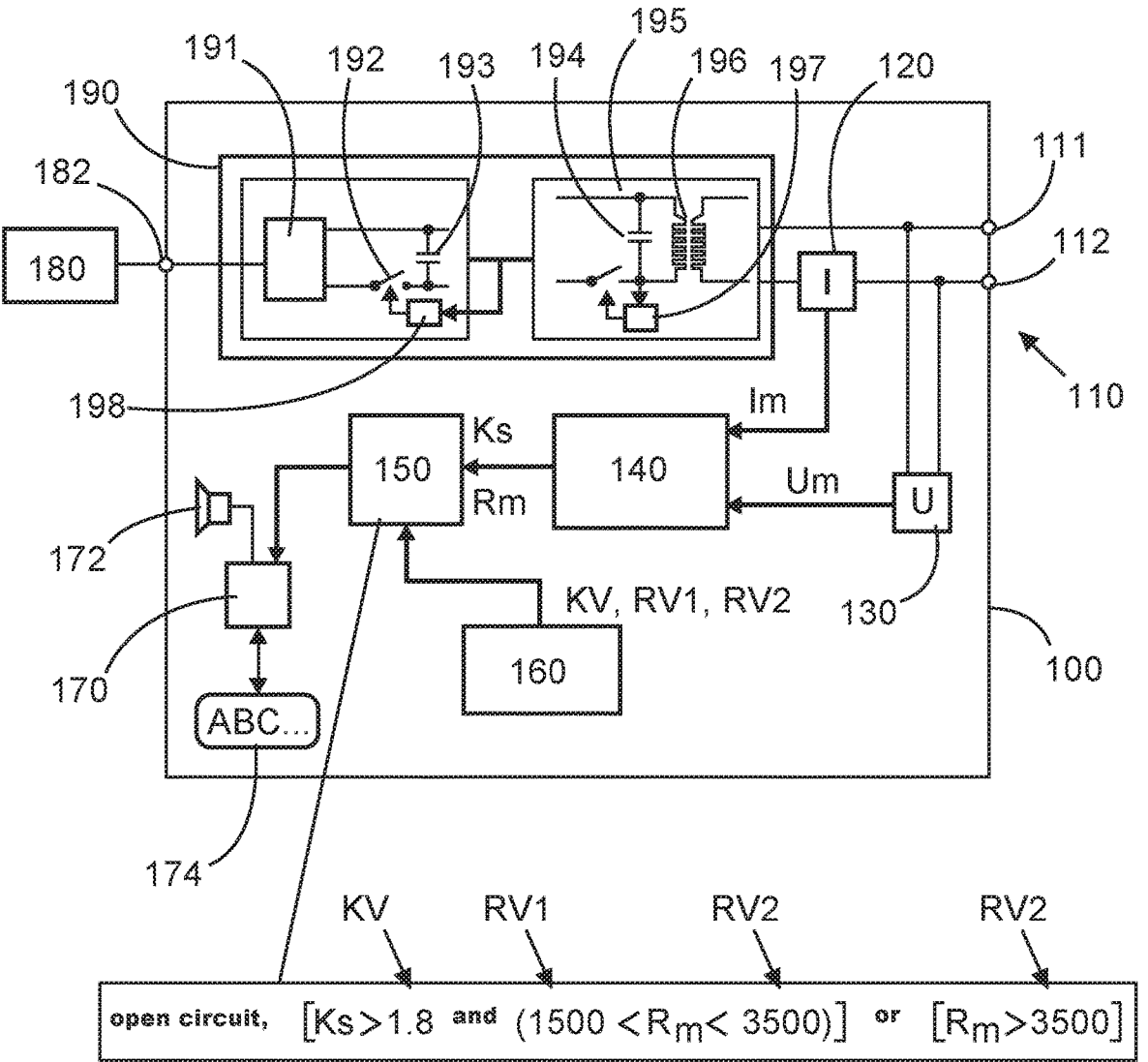
FIG. 3 shows a schematic construction of an electrosurgical generator according to the invention.

FIG. 3 shows a schematic construction of an electrosurgical generator 100 according to the invention in more detail.

The generator 100 includes an instrument terminal 110 for connecting and electrically supplying the electrosurgical instrument 200. The instrument terminal 110 includes two terminal contacts 111 and 112. The instrument terminal 110 can also be understood as connection socket.

The generator 100 includes for electrically supplying the electrosurgical instrument 200 a supply terminal 182 for connecting the generator 100 with an electrical supply grid 180. The electrical supply grid 180 may be a public supply grid. The generator 100 includes a power converter 190, which is used to convert the input current and the input voltage of the supply grid into a suitable operation current and/or operation voltage at the instrument terminal 110. The power converter 190 can also be understood as a switching power supply. Power converters for converting alternating current to direct current are known as rectifiers. Power converters for converting direct current to alternating current are known as inverted rectifier or inverters. Power converters for converting one AC current to another AC current are known as frequency converters. Power converters for converting one direct current to another direct current are known as DC-to-DC converters. The generated alternating current or generated direct current can be higher, lower or inverted depending on the design of the converter or the requirements of the electrical load, respectively the electrosurgical instrument. The shown power converter is an inverter that is adapted to convert the AC current from the grid into an AC operation current at the terminal 110 for electrical supplying the instrument 200 with an alternating current, respectively alternating voltage. However it is understood, that in case the instrument works with direct current, the power converter would be implemented as a DC-to-DC converter. The power converter 190 includes a rectifier device 191 in order to rectify the drawn alternating voltage from the grid into an intermediate circuit DC voltage. The rectifier 190 is for example a passive or active rectifier. The capacitor 193, 194 is an intermediate capacitor and is used as temporal energy buffer. The power converter 190 also includes a converter device 195 for generating the operation current and/or operation voltage at the instrument terminal 110, with the desired amplitude and frequency. The converter device 195 for example includes semiconductor switches such as IGBTs, MOSFETS or the like, which are arranged in a half-bridge topology or the like. The converter 195 may also include a transformer 196, for example a step-up-transformer, in order to step up the voltage at the instrument terminal into a voltage with a desired amplitude and or frequency. In general, the power converter 190 is adapted to generate a high frequency current for supplying the instrument 200 with power. The power converter 190 also includes driver circuits 197, 198 for controlling electrical switches, for example the electrical switch 192.

The driver circuits 197, 198 and the switches illustrate that the power converter 190 may include a step up converter or the like, depending on the type of power converter 190. In case the power converter 190 is an AC-to-AC converter the driver circuits 197, 198 and the switches 192 illustrate that the power converter 190 includes controllable switches in order to generate the output current and output current at the instrument terminal 110.

The generator 100 also includes a current measuring device 120 for determining a current $I_m$ at the instrument terminal 110 and a voltage measuring device 130 for determining a voltage $U_m$ at the instrument terminal 110 in order to determine the high resistance condition.

The electrosurgical generator 100 also includes a calculation device 140 connected to the current measuring device 120 and voltage measuring device 130 and which is configured to evaluate the determined current and the determined voltage. The calculation device 140 receives the determined voltage $U_m$ and $I_m$ from the measuring devices 120 and 130. I indicates current. U indicates voltage. R indicates resistance or impedance.

The calculation device 140 is adapted to determine a crest factor value $K_S$ and a resistance $R_m$ from the determined current $I_m$ and/or the determined voltage $U_m$. The determined values $K_S$ and $R_m$ are inputted into the comparison device 150.

The crest factor value $K_S$ describes a ratio of a peak value $I_{peak}$ or $U_{peak}$ to an effective value $I_{RMS}$ or $U_{RMS}$ of the determined current $I_m$ and/or the determined voltage $U_m$. RMS stands for root square mean.

The electrosurgical generator 100 also includes a comparison device 150 for comparing the determined crest factor value $K_S$ and the determined resistance value $R_m$ with a crest factor comparison value $K_V$ and a first and second resistance comparison values $R_{V1}$ and $R_{V2}$, wherein the crest factor comparison value $K_V$ and the first and second resistance comparison values $R_{V1}$ and $R_{V2}$ are stored in a data storage device 160 of the electrosurgical generator 100 in order to carry out the comparison.

FIG. 3 also shows as an example of the condition that has to be fulfilled when an open circuit is detected with the comparison device 150. An open circuit is indicated when $K_S$ is greater than 1.8 and $R_m$ is between $R_{V1}$=1500 Ohm and $R_{V2}$=3500 ohm or $R_m$ is greater than $R_{V2}$=3500.

$$[K_S > 1.8 \text{ and } (1500 < R_m < 3500)] \text{ or } [R_m > 3500]$$

The electrosurgical generator 100 also includes a signaling device 170 for signaling the high resistance condition when the said condition is fulfilled. Thereby, the signaling device 170 comprises an acoustic signaling device 172 for outputting an acoustic signal to acoustically signal the high resistance condition detected at the instrument terminal 110 when said condition is fulfilled, namely a speaker 172 and the signaling device 170 comprises an optical signaling device 174 for outputting an optical signal or message to optically signal the high resistance condition detected at the instrument terminal 110 when said condition is fulfilled, namely the display 174, as shown for example in FIG. 1.

Figure 4:
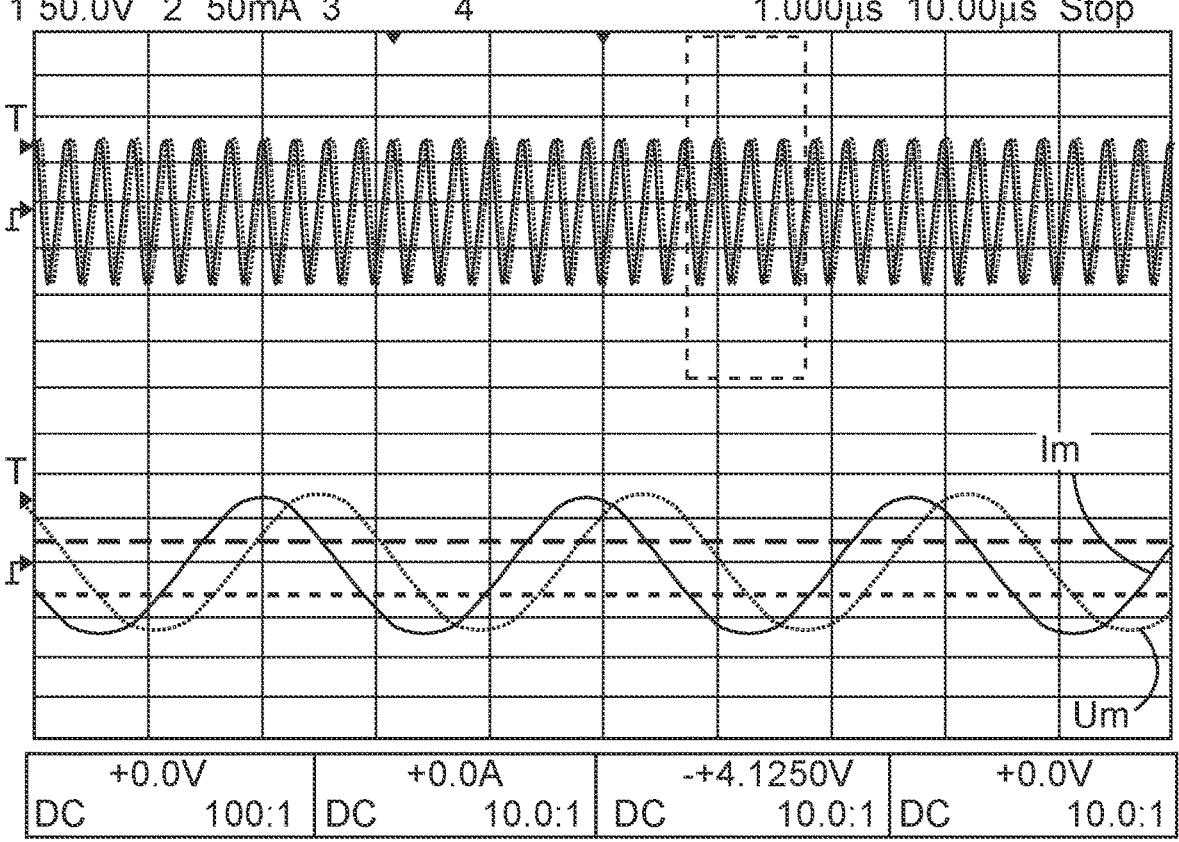
FIG. 4 shows an undistorted waveform of a determined voltage and current.

FIG. 4 shows an undistorted waveform of a determined voltage $U_m$ and current $I_m$. As can be seen, the waveforms of the voltage $U_m$ and the current $I_m$ having an essentially sinusoidal or cosinusoidal shape. Only small ripples can be observed in the course of the waveforms, caused by the on and off switching of the switches or transistors of the power converter. The calculated crest factor $K_S$ is in this example 1.5.

Figure 5:
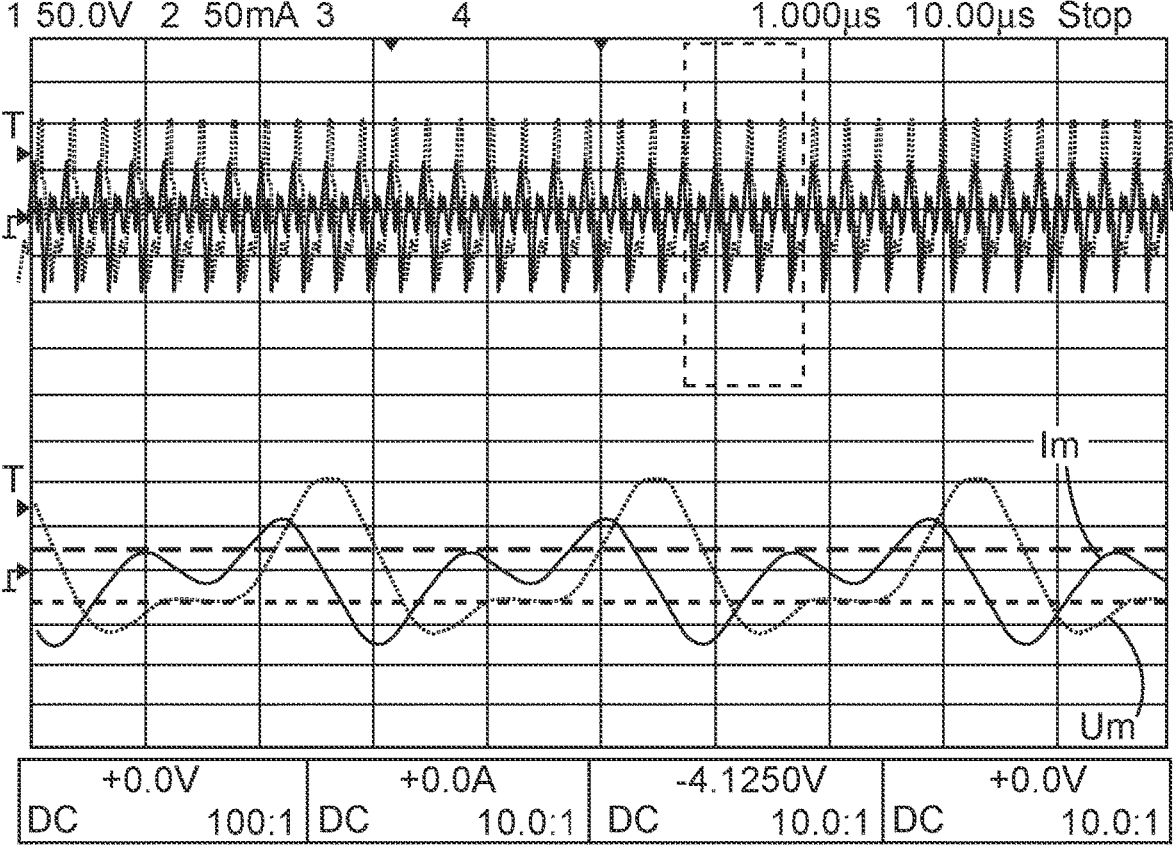
FIG. 5 shows a distorted waveform of a determined voltage and current.

FIG. 5 shows a distorted waveform of a determined voltage $U_m$ and current $I_m$. As can be seen, the waveforms of the voltage $U_m$ and the current $I_m$ having a harmonic distorted shape. Strong harmonics overlay the voltage $U_m$ and the current $I_m$ that could be cause by a unfavorable capacitive load. The calculated crest factor value $K_S$ for this signal is in this example 2. When comparing FIGS. 4 and 5 it is obvious that the crest factor value $K_S$ in the distorted case is higher than in the undistorted case.

Figure 6:
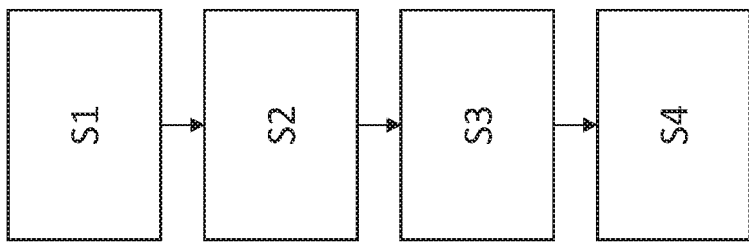
FIG. 6 shows a schematic flow chart of the method for monitoring a high resistance condition at an instrument terminal of an electrosurgical generator in an embodiment.

FIG. 6 shows a schematic flow chart of the method for monitoring a high resistance condition at an instrument terminal of an electrosurgical generator.

In step S1 determining a current $I_m$ and a voltage $U_m$ at the instrument terminal 110 is performed by means of a current measuring device 120 and a voltage measuring device 130.

In step S2 determining a crest factor value $K_S$ from the determined current $I_m$ and/or the determined voltage $U_m$ with a calculation device 140 is performed, wherein the crest factor value describes a ratio of a peak value $I_{peak}$; $U_{peak}$ to an effective value $I_{RMS}$; $U_{RMS}$ of the determined current $I_m$ and/or the determined voltage $U_m$.

In step S3 comparing the determined crest factor value $K_S$ with a crest factor comparison value $K_V$ is performed by means of a comparison device 150 of the electrosurgical generator 100, wherein the crest factor comparison value $K_V$ is stored in a data storage device 160 of the electrosurgical generator 100 for performing the comparison.

In step S4 signaling a high resistance condition with a signaling device 170 of the electrosurgical generator is performed when the determined crest factor $K_S$ reaches or exceeds $K_S \geq K_V$ the predetermined crest factor comparison value $K_V$.

Step S2 preferably also include the step: Determining a resistance value $R_m$ from the determined current $I_m$ and/or the determined voltage $U_m$ with the calculation device 140.

Step S3 preferably also includes the step: Comparing the determined resistance value $R_m$ with a first resistance comparison value $R_{V1}$ and/or a second resistance comparison value $R_{V2}$ with the comparison device 150, wherein the first resistance comparison value $R_{V1}$ defines a lower limit for the determined resistance $R_m$ and the second resistance comparison value $R_{V2}$ defines an upper limit for the determined resistance $R_m$, and wherein for performing the comparison the first resistance comparison value $R_{V1}$ and/or the second resistance comparison value $R_{V1}$ is stored in the data storage device 160.

Step S4 preferably also includes the steps: signaling the high resistance condition with a signaling device 170 of the electrosurgical generator when the determined crest factor $K_S$ reaches or exceeds ($K_S \geq K_V$) the predetermined crest factor comparison value $K_V$ and when the determined resistance value $R_m$ is between the first resistance comparison value and the second resistance comparison value ($R_{V1} < R_m < R_{V2}$) and signaling the high resistance condition with a signaling device 170 of the electrosurgical generator when the determined resistance value $R_m$ exceeds the second resistance comparison value ($R_m > R_{V2}$).

The generator, generator system and method described above offer a number of advantages, which are summarized below:

Reliable detection of open circuits, no contact with tissue or an interrupted line (cable break)

Detection possible especially for bad waveforms

Simple implementation due to already existing sensors

LIST OF REFERENCE SIGNS

10 Electrosurgical generator system
100 Electrosurgical generator
102 Operating device
110 Instrument terminal
111, 112 Terminal contact
120 Current measuring device
130 Voltage measuring device
140 Calculation device
150 Comparison device
160 Data storage device
170 Signaling device
172 Acoustic signaling device
174 Optical signaling device
180 Electrical supply grid
182 Supply terminal
190 Power converter
191 Rectifier device
192 Switch
193, 194 Capacitor
195 Converter device
196 Transformer
197, 198 Driver circuit
200 Electrosurgical instrument
202 Connection line
204 Tissue
$I_m$ current value
$U_m$ voltage value
$K_S$ crest factor value
$K_V$ crest factor comparison value
$R_m$ resistance value
$R_{V1}$, $R_{V2}$ Resistance comparison value

The invention claimed is:

1. A method for monitoring a high resistance condition at an instrument terminal of an electrosurgical generator, wherein:

the instrument terminal being adapted for connecting and electrically supplying an electrosurgical instrument;

the electrosurgical generator includes a current measuring device for determining a current at the instrument terminal and a voltage measuring device for determining a voltage at the instrument terminal in order to determine the high resistance condition; and the electrosurgical generator includes a calculation device connected to the current measuring device and the voltage measuring device and which is configured to evaluate the determined current and a determined voltage, comprising:

determining a crest factor value from the determined current and/or the determined voltage with the calculation device, wherein the crest factor value describes a ratio of a peak value to an effective value of the determined current and/or the determined voltage;

comparing a determined crest factor value with a crest factor comparison value by means of a comparison device of the electrosurgical generator, wherein the crest factor comparison value is stored in a data storage device of the electrosurgical generator for performing a comparison:

signaling the high resistance condition with a signaling device of the electrosurgical generator when the determined crest factor value reaches or exceeds a predetermined crest factor comparison value; and determining a resistance value from the determined current and/or the determined voltage with the calculation device;

comparing a determined resistance value with first resistance comparison value and/or a second resistance comparison value with the comparison device, wherein:

the first resistance comparison value defines a lower limit for the determined resistance value, the second resistance comparison value defines an upper limit for a determined resistance;

when performing a comparison of the determined resistance value with the first resistance comparison value and/or a second resistance comparison value, the first resistance comparison value and/or the second resistance comparison value is stored in the data storage device; and signaling the high resistance condition with the signaling device of the electrosurgical generator when the determined crest factor reaches or exceeds the predetermined crest factor comparison value and the second resistance comparison value.

2. The method according claim 1, wherein signaling the high resistance condition is additionally performed when the determined resistance value exceeds the second resistance comparison value.

3. The method according to claim 1, wherein:

the first resistance comparison value is in a resistance range between 1000 ohms to 2000 ohms; and/or the second resistance comparison value is in a resistance range between 3000 ohms to 5000 ohms.

4. The method according to claim 1, wherein the crest factor comparison value ($K_V$) comprises:

at least $1.25*\sqrt{2}(K_V>1.25*\sqrt{2})$ for a substantially sinusoidal current generated by the electrosurgical generator at the instrument terminal;

at least $1.25*\sqrt{3}(K_V>1.25*\sqrt{3})$ for a substantially triangular current generated with the electrosurgical generator at the instrument terminal; and/or at least $1.25*\sqrt{1}(K_V>1.25*\sqrt{1})$ for a substantially rectangular current generated with the electrosurgical generator at the instrument terminal.

5. The method according to claim 1, wherein:

a signaling device comprises an acoustic signaling device for outputting an acoustic signal to acoustically signal the high resistance condition detected at the instrument terminal when at least the determined crest factor reaches or exceeds the crest factor comparison value; and/or the signaling device comprises an optical signaling device for outputting an optical signal or message to optically signal the high resistance condition detected at the instrument terminal when at least the determined crest factor reaches or exceeds the crest factor comparison value.

6. The method according to claim 1, wherein the electrosurgical generator is a high frequency generator and the determined current and the determined voltage are alternating quantities.

7. The method according to claim 1, wherein:
the electrosurgical generator comprises a plurality of
   instrument terminals;
the high resistance condition of each of the instrument
   terminals is monitored by determining the current and/
   or the voltage at each of the instrument ten terminals,
   the method comprising:
determining a crest factor for each instrument terminal;
   and
comparing each crest factor with the crest factor com-
   parison value.
8. An electrosurgical generator adapted to monitor a high
resistance condition at an instrument terminal of the elec-
trosurgical generator, wherein:
   the instrument terminal is adapted for connecting and
      electrically supplying the electrosurgical instrument;
   the electrosurgical generator includes a current measuring
      device for determining a current at the instrument
      terminal and a voltage measuring device for determin-
      ing a voltage at the instrument terminal in order to
      determine the high resistance condition;
   the electrosurgical generator includes a calculation device
      which is connected to the current measuring device and
      the voltage measuring device and which is configured
      to evaluate the determined current and the determined
      voltage;
   the calculation device is adapted to determine a crest
      factor value from the determined current and the deter-
      mined voltage, wherein the crest factor value describes
      a ratio of a peak value to an effective value of the
      determined current and/or the determined voltage;
   the electrosurgical generator comprises a comparison
      device for comparing the determined crest factor value
      with a crest factor comparison value, wherein the crest
      factor comparison value is stored in a data storage
      device of the electrosurgical generator for performing
      the comparison;
   the electrosurgical generator comprises a signaling device
      for signaling the high resistance condition, wherein the
      high resistance condition is signaled with the signaling
      device when a determined crest factor reaches or
      exceeds a predetermined crest factor comparison value;
   the calculation device is also adapted for determining
      resistance value from the determined current and/or the
      determined voltage;
   the comparison device is adapted for comparing the
      determined resistance value with a first resistance com-
      parison value and/or a second resistance comparison
      value with the comparison device;
   the first resistance comparison value defines a lower limit
      for the determined resistance; an
   the second resistance comparison value defines an upper
      limit for the determined resistance;
   when performing a comparison of the determined resis-
      tance value with the first resistance comparison value
      and/or a second resistance comparison value, the first resistance comparison value and/or the second resis-
      tance comparison value is stored in the data storage
      device; and
   the high resistance condition is signaled with the signaling
      device when the determined crest factor reaches or
      exceeds the predetermined crest factor comparison
      value and when the determined resistance value is
      between the first resistance comparison value and the
      second resistance comparison value.
9. The electrosurgical generator according to claim 8,
wherein the electrosurgical generator is a high frequency
generator and the determined current and the determined
voltage are alternating quantities.
10. An electrosurgical generator system comprising an
electrosurgical generator, comprising:
   at least one instrument terminal for connecting and elec-
      trically supplying the electrosurgical instrument,
      wherein:
      in operation of the electrosurgical generator system the
         electrosurgical instrument is connected to the instru-
         ment terminal;
      the electrosurgical generator is configured according to
         claim 8 and/or is adapted to perform a method for
         monitoring the high resistance condition at the
         instrument terminal of the electrosurgical generator,
         according to claim 8;
      the instrument terminal being adapted for connecting
         and electrically supplying the electrosurgical instru-
         ment;
      the electrosurgical generator includes the current mea-
         suring device for determining a current at the instru-
         ment terminal and the voltage measuring device for
         determining a voltage at the instrument terminal in
         order to determine the high resistance condition; and
   the electrosurgical generator includes the calculation
      device connected to the current measuring device and
      the voltage measuring device and which is configured
      to evaluate the determined current and the determined
      voltage, comprising:
      determining the crest factor value from the determined
         current and/or the determined voltage with the cal-
         culation device, wherein the crest factor value
         describes a ratio of a peak value to an effective value
         of the determined current and/or the determined
         voltage;
      comparing the determined crest factor value with the
         crest factor comparison value by means of the com-
         parison device of the electrosurgical generator,
         wherein the crest factor comparison value is stored in
         the data storage device of the electrosurgical gen-
         erator for performing the comparison; and
      signaling the high resistance condition with the signal-
         ing device of the electrosurgical generator when the
         determined crest factor reaches or exceeds the pre-
         determined crest factor comparison value.

* * * * *